(12) United States Patent
Bryans et al.

(10) Patent No.: US 6,489,352 B2
(45) Date of Patent: Dec. 3, 2002

(54) CONFORMATIONALLY CONSTRAINED COMPOUNDS AS PHARMACEUTICAL AGENTS

(75) Inventors: Justin Stephen Bryans, Balsham (GB); David Christopher Horwell, Cambridge (GB); Jean-Marie Receveur, Cambridge (GB)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/924,803

(22) Filed: Aug. 8, 2001

(65) Prior Publication Data

US 2002/0019540 A1 Feb. 14, 2002

Related U.S. Application Data

(62) Division of application No. 09/622,429, filed as application No. PCT/US99/09134 on Apr. 28, 1999, now Pat. No. 6,316,638.
(60) Provisional application No. 60/086,694, filed on May 26, 1998.

(51) Int. Cl.$^7$ .................... C07D 209/54; A61K 31/403
(52) U.S. Cl. ......................... 514/409; 548/441
(58) Field of Search ............................ 514/409; 548/411

(56) References Cited

U.S. PATENT DOCUMENTS

| | | | |
|---|---|---|---|
| 4,024,175 A | 5/1977 | Satzinger et al. | 260/468 J |
| 4,087,544 A | 5/1978 | Satzinger et al. | 424/305 |
| 5,286,723 A | 2/1994 | Hayakawa et al. | 514/213 |
| 5,510,381 A | 4/1996 | Pande | 514/561 |

FOREIGN PATENT DOCUMENTS

| | | |
|---|---|---|
| WO | 9603122 | 2/1996 |
| WO | 9733859 | 9/1997 |

OTHER PUBLICATIONS

PCT International Search Report, PCT/US99/09134, Aug. 2000.
Bryans et al., "Investigation into the preferred conformation of gabapentin for interaction with its binding site on the alpha2delta subunit of a calcium channel", *Bioorganic & Medicinal Chemistry Letters*, vol. 7, No. 19, 1997, pp. 2481–2484.
Wermuth, "Chemical aspects of pro–drug design", *Chemistry and Industry*, 1980, pp. 433–435.
Palomino, "Delivery of drugs through dihydropyridine carriers", *Drugs of the Future*, vol. 15, No. 4, 1990, pp. 361–368.
Mellick and Seng, "The use of gabapentin in the treatment of reflex sympathetic dystrophy and a phobic disorder", *AJPM*, vol. 5, No. 1, 1995, pp. 7–9.

Primary Examiner—John M. Ford
(74) Attorney, Agent, or Firm—Charles W. Ashbrook; Elizabeth M. Anderson; David R. Kurlandsky

(57) ABSTRACT

Novel substituted amino acids of formula

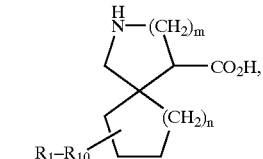

(I)

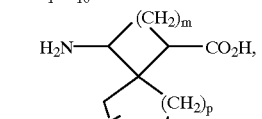

(II)

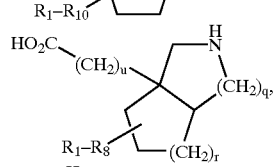

(III)

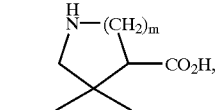

(IV)

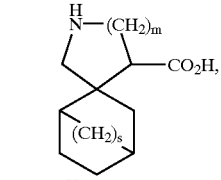

(V)

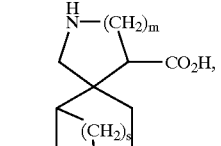

(VI)

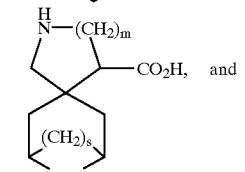

(VII)

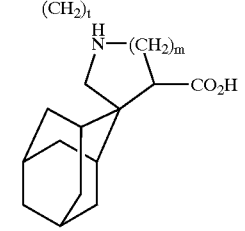

(VIII)

are disclosed and are useful as agents in the treatment of epilepsy, faintness attacks, hypokinesia, cranial disorders, neurodegenerative disorders, depression, anxiety, panic, pain, and neuropathological disorders. Processes for the preparation and intermediates useful in the preparation are also disclosed.

4 Claims, No Drawings

CONFORMATIONALLY CONSTRAINED COMPOUNDS AS PHARMACEUTICAL AGENTS

CROSS REFERENCE TO RELATED APPLICATIONS

This application is a divisional of U.S. Ser. No. 09/622,429 filed Aug. 16, 2000, now U.S. Pat. No. 6,316,638, which is a 371 filing of PCT/US99/09134 filed Apr. 28, 1999, priority based on Provisional Application No. 60/086,694 filed May 26, 1998.

BACKGROUND OF THE INVENTION

Compounds of formula

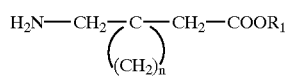

wherein $R_1$ is hydrogen or a lower alkyl radical and n is 4, 5, or 6 are known in U.S. Pat. No. 4,024,175 and its divisional U.S. Pat. No. 4,087,544. The uses disclosed are: protective effect against cramp induced by thiosemicarbazide; protective action against cardiazole cramp; the cerebral diseases, epilesy, faintness attacks, hypokinesia, and cranial traumas; and improvement in cerebral functions. The compounds are useful in geriatric patients. The patents are hereby incorporated by reference.

SUMMARY OF THE INVENTION

The compounds, prodrugs, and pharmaceutically acceptable salts are useful in a variety of disorders. The disorders include: epilepsy, faintness attacks, hypokinesia, cranial disorders, neurodegenerative disorders, depression, anxiety, panic, pain, and neuropathological disorders.

The compounds are those of formula

I
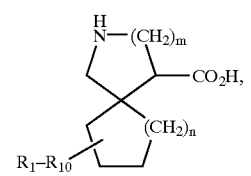

II
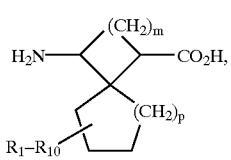

III
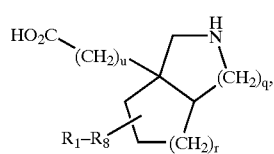

IV
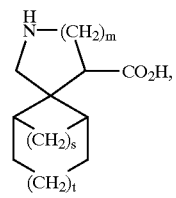

V
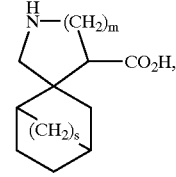

VI
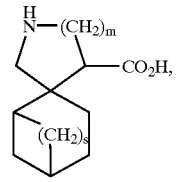

VII
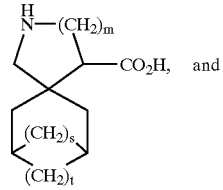

VIII
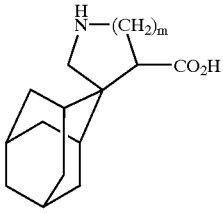

or a pharmaceutically acceptable salt thereof or a prodrug thereof wherein $R_1$ to $R_{10}$ are each independently selected from hydrogen or a straight or branched alkyl of from 1 to 6 carbons, benzyl, or phenyl;

m is an integer of from 0 to 3;
n is an integer of from 1 to 2;
o is an integer of from 0 to 3;
p is an integer of from 1 to 2;
q is an integer of from 0 to 2;
r is an integer of from 1 to 2;
s is an integer of from 1 to 3;
t is an integer of from 0 to 2; and
u is an integer of from 0 to 1.

Novel intermediates useful in the preparation of the final compounds are, for example:

2-Benzyl-2-aza-spiro[4.5]decane-4,4-dicarboxylic acid dimethyl ester hydrochloride;

2-Aza-spiro[4.5]decane-4,4-dicarboxylic acid dimethyl ester hydrochloride;

1-Benzyloxymethyl-2-aza-spiro[3.5]nonane-2-carboxylic acid tert-butyl ester;

1-Hydroxymethyl-2-aza-spiro[3.5]nonane-2-carboxylic acid tert-butyl ester;

2-Aza-spiro[3.5]nonane-1,2-dicarboxylic acid 2-tert-butyl ester;

[3aS-(3α7aα)]-7a-tert-Butoxycarbonylmethyl-1-oxo-octahydro-isoindole-2-carboxylic acid tert-butyl ester; and

[3aS-(α7aα)]-3a-tert-Butoxycarbonylmethyl-octahydro-isoindole-2-carboxylic acid tert-butyl ester.

DETAILED DESCRIPTION OF THE INVENTION

The compounds of the instant invention and their pharmaceutically acceptable salts and prodrugs are as defined by Formula I to VIII above.

Preferred compounds are those of Formula I above.

Especially preferred are those of Formula I wherein $R_1$ to $R_{10}$ is hydrogen;

m is of from 0to 3, and n is 1 or 2.

More especially preferred are those compounds selected from:

(±)-2-Aza-spiro[3.5]nonane-1-carboxylic acid hydrochloride;

(±)-2-Aza-spiro[4.5]decane-4-carboxylic acid hydrochloride;

(R)-2-Aza-spiro[4.5]decane-4-carboxylic acid hydrochloride;

(S)-2-Aza-spiro[4.5]decane-4-carboxylic acid hydrochloride; and (R)-2-Aza-spiro[4.5]decane4-carboxylic acid.

Other preferred compounds are those of Formula II above.

Especially preferred are those of Formula II wherein $R_1$ to $R_{10}$ is hydrogen, o is from 0 to 3; and, p is 1 to 2.

Other preferred compounds are those of Formula III above wherein $R_1$ to $R_{10}$ is hydrogen, q is from 0 to 2; and r is 1 to 2.

Especially preferred is (±)-[3aS-(3α7aα)]-(Octahydro-isoindol-3a-yl)-acetic acid trifluoroacetate.

Also especially preferred are compounds selected from:

7-Methyl-2-aza-spiro[4.4]nonane-4-carboxylic acid;

[4α,5β(R*)]7-Methyl-2-aza-spiro[4.5]decane-4-carboxylic acid;

[4α,5α(S*)]7-Methyl-2-aza-spiro[4.5]decane-4-carboxylic acid;

[4α,5α(R*)]7-Methyl-2-aza-spiro[4.5]decane-4-carboxylic acid;

[4α,5β(S*)]7-Methyl-2-aza-spiro[4.5]decane-4-carboxylic acid;

7,8-Dimethyl-2-aza-spiro[4.4]nonane-4-carboxylic acid;

7-Methyl-2-aza-spiro[4.5]decane-4-carboxylic acid;

7,9-Dimethyl-2-aza-spiro[4.5]decane-4-carboxylic acid;

Spiro[bicyclo[3.3.1]nonane-9,3'-pyrrolidine]-4'-carboxylic acid;

Spiro[pyrrolidine-3,2'-tricyclo[3.3.1.1$^{3,7}$]decane]-4-carboxylic acid;

3-Amino-6-methyl-spiro[3.5]nonane-1-carboxylic acid;

3-Amino-6,8-dimethyl-spiro[3.5]nonane-1-carboxylic acid;

4-Amino-7-methyl-spiro[4.5]decane-1-carboxylic acid;

4-Amino-7,9-dimethyl-spiro[4.5]decane-1-carboxylic acid;

3-Amino-6-methyl-spiro[3.4]octane-1-carboxylic acid;

3-Amino-6,7-dimethyl-spiro[3.4]octane-1-carboxylic acid;

4-Amino-7-methyl-spiro[4.4]nonane-1-carboxylic acid; and

4-Amino-7,8-dimethyl-spiro[4.4]nonane-1-carboxylic acid.

Pharmaceutical compositions comprising a therapeutically effective amount of a compound of Formulas I–VIII above are included in the instant invention.

Methods of using the compounds of the invention as agents for treating epilepsy, faintness attacks, hypokinesia, cranial disorders, neurodegenerative disorders, depression, anxiety, panic, pain, and neuropathological disorders are part of the invention, The term "alkyl" is a straight or branched group of from 1 to 6 carbon atoms including but not limited to methyl, ethyl, propyl, n-propyl, isopropyl, butyl, 2-butyl, tert-butyl, pentyl, hexyl, and n-hexyl.

Preferred groups are methyl and tert-butyl.

The benzyl and phenyl groups may be unsubstituted or substituted by from 1 to 3 substituents selected from halogen, alkyl, alkoxy, hydroxy, carboxy, carboalkoxy, trifluoromethyl, and nitro.

Halogen includes fluorine, bromine, chlorine, and iodine.

Since amino acids are amphoteric, pharmacologically compatible salts when R is hydrogen can be salts of appropriate inorganic or organic acids, for example, hydrochloric, sulphuric, phosphoric, acetic, oxalic, lactic, citric, malic, salicylic, malonic, maleic, succinic, and ascorbic. Starting from corresponding hydroxides or carbonates, salts with alkali metals or alkaline earth metals, for example, sodium, potassium, magnesium, or calcium are formed. Salts with quaternary ammonium ions can also be prepared with, for example, the tetramethyl-ammonium ion.

Prodrugs of compounds I–VIII are included in the scope of the instant invention. Aminoacyl-glycolic and -lactic esters are known as prodrugs of amino acids (Wermuth C. G., *Chemistry and Industry*, 1980:433–435). The carbonyl group of the amino acids can be esterified by known means. Prodrugs and soft drugs are known in the art (Palomino E., *Drugs of the Future*, 1990;15(4):361–368). The last two citations are hereby incorporated by reference.

The effectiveness of an orally administered drug is dependent upon the drug's efficient transport across the mucosal epithelium and its stability in enterohepatic circulation. Drugs that are effective after parenteral administration but less effective orally, or whose plasma half-life is considered too short, may be chemically modified into a prodrug form.

A prodrug is a drug which has been chemically modified and may be biologically inactive at its site of action, but which may be degraded or modified by one or more enzymatic or other in vivo processes to the parent bioactive form.

This chemically modified drug, or prodrug, should have a different pharmacokinetic profile to the parent, enabling easier absorption across the mucosal epithelium, better salt formulation and/or solubility, improved systemic stability (for an increase in plasma half-life, for example). These chemical modifications may be 1) ester or amide derivatives which may be cleaved by, for example, esterases or lipases. For ester derivatives, the ester is derived from the carboxylic acid moiety of the drug molecule by known means. For amide derivatives, the amide may be derived from the carboxylic acid moiety or the amine moiety of the drug molecule by known means.

2) peptides which may be recognized by specific or nonspecific proteinases. A peptide may be coupled to the drug molecule via amide bond formation with the amine or carboxylic acid moiety of the drug molecule by known means.

3) derivatives that accumulate at a site of action through membrane selection of a prodrug form or modified prodrug form, 4) any combination of 1 to 3.

Current research in animal experiments has shown that the oral absorption of certain drugs may be increased by the preparation of "soft" quaternary salts. The quaternary salt is termed a "soft" quaternary salt since, unlike normal quaternary salts, e.g., $R—N+(CH_3)_3$, it can release the active drug on hydrolysis.

"Soft" quaternary salts have useful physical properties compared with the basic drug or its salts. Water solubility may be increased compared with other salts, such as the hydrochloride, but more important there may be an increased absorption of the drug from the intestine. Increased absorption is probably due to the fact that the "soft" quaternary salt has surfactant properties and is capable of forming micelles and unionized ion pairs with bile acids, etc., which are able to penetrate the intestinal epithelium more effectively. The prodrug, after absorption, is rapidly hydrolyzed with release of the active parent drug.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures. thereof. For example, the compound of Example 1 is a mixture of all four possible stereoisomers. The compound of Example 6 is one of the isomers. The configuration of the cyclohexane ring carbon centers may be R or S in these compounds where a configuration can be defined.

The radioligand binding assay using [$^3$H]gabapentin and the $\alpha_2\delta$ subunit derived from porcine brain tissue was used (Gee N. S., Brown J. P., Dissanayake V. U. K., Offord J., Thurlow R., Woodruff G. N., "The Novel Anti-convulsant Drug, Gabapentin, Binds to the $\alpha_2\delta$ Subunit of a Calcium Channel," *J. Biol. Chem.*, 1996;271:5879–5776).

TABLE 1

| Compound | Structure | IC$_{50}$ ($\mu$M) at $\alpha_2\delta$ Binding Site |
|---|---|---|
| (±)-2-Aza-spiro[4.5]decane-4-carboxylic acid hydrochloride | HCl·HN—[structure]—CO$_2$H | 0.35 |
| (R)-2-Aza-spiro[4.5]decane-4-carboxylic acid hydrochloride | HCl·HN—[structure]—""CO$_2$H | 0.16 |
| (S)-2-Aza-spiro[4.5]decane-4-carboxylic acid hydrochloride | HCl·HN—[structure]—CO$_2$H | >10 |
| (±)-2-Aza-spiro[3.5]nonane-1-carboxylic acid hydrochloride | HCl·HN—[structure]—CO$_2$H | 1.5 |
| (±)-[3aS-(3α,7aα)]-(Octahydro-isoindol-3a-yl)-acetic acid trifluoroacetate | HO$_2$C—[structure]—NH·HO$_2$CCF$_3$ | >10 |

TABLE 1-continued

| Compound | Structure | IC$_{50}$ ($\mu$M) at $\alpha_2\delta$ Binding Site |
|---|---|---|
| Spiro[pyrrolidine-3,2'-tricyclo[3.3.1.1$^{3,7}$]decane]-4-carboxylic acid | 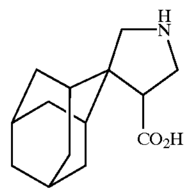 | 0.42 |
| Spiro[bicyclo[3.3.1]nonane-9,3'-pyrrolidine]-4'-carboxylic acid | 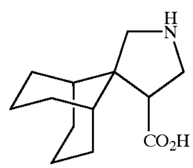 | 0.57 |

Table 1 above shows the binding affinity of the compounds of the invention to the $\alpha_2\delta$ Subunit.

The compounds of the invention are compared to Neurontin®, a marketed drug effective in the treatment of such disorders as epilepsy. Neurontin® is 1-(aminomethyl)-cyclohexaneacetic acid of structural formula

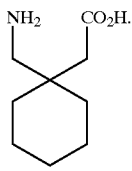

Gabapentin (Neurontin®) is about 0.10 to 0.12 $\mu$M in this assay. The compounds of the instant invention are expected, therefore, to exhibit pharmacologic properties comparable to gabapentin. For example, as agents for convulsions, anxiety, and pain.

The present invention also relates to therapeutic use of the compounds of the mimetic as agents for neurodegenerative disorders.

Such neurodegenerative disorders are, for example, Alzheimer's disease, Huntington's disease, Parkinson's disease, and Amyotrophic Lateral Sclerosis.

The present invention also covers treating neurodegenerative disorders termed acute brain injury. These include but are not limited to: stroke, head trauma, and asphyxia.

Stroke refers to a cerebral vascular disease and may also be referred to as a cerebral vascular incident (CVA) and includes acute thromboembolic stroke. Stroke includes both ,focal and global ischemia. Also, included are transient cerebral ischemic attacks and other cerebral vascular problems accompanied by cerebral ischemia. A patient undergoing carotid endarterectomy specifically or other cerebrovasculatr or vascular surgical procedures in general, or diagnostic vascular procedures including cerebral angiography and the like.

Other incidents are head trauma, spinal cord trauma, or injury from general anoxia, hypoxia, hypoglycemia, hypotension as well as similar injuries seen during procedures from embole, hyperfusion, and hypoxia.

The instant invention would be useful in a range of incidents, for example, during cardiac bypass surgery, in incidents of intracranial hemorrhage, in perinatal asphyxia, in cardiac arrest, and status epilepticus.

Pain refers to acute as well as chronic pain.

Acute pain is usually short-lived and is associated with hyperactivity of the sympathetic nervous system. Examples are postoperative pain and allodynia.

Chronic pain is usually defined as pain persisting from 3 to 6 months and includes somatogenic pains and psychogenic pains. Other pain is nociceptive.

Still other pain is caused by injury or infection of peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Neuropathic pain includes, but is not limited to pain caused by nerve injury such as, for example, the pain diabetics suffer from.

Psychogenic pain is that which occurs without an organic origin such as low back pain, atypical facial pain, and chronic headache.

Other types of pain are: inflammatory pain, osteoarthritic pain, trigeminal neuralgia, cancer pain, diabetic neuropathy, restless leg syndrome, acute herpetic and postherpetic neuralgia, causalgia, brachial plexus avulsion, occipital neuralgia, gout, phantom limb, burn, and other forms of neuralgia, neuropathic and idiopathic pain;syndrome.

A skilled physician will be able to determine the appropriate situation in which subjects are susceptible to or at risk of, for example, stroke as well as suffering from stroke for administration by methods of the present invention.

The compounds of the invention are also expected to be useful in the treatment of depression. Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the Diagnostic and Statistical Manual of Mental Disorders (Fourth Edition) referred to as the DSM-IV-R manual published by the American Psychiatric Association, 1994.

GABA is an inhibitory neurotransmitter with the central nervous system. Within the general context of inhibition, it seems likely that GABA-mimetics might decrease or inhibit cerebral function and might therefore slow function and decrease mood leading to depression.

The compounds of the instant invention may produce an anticonvulsant effect through the increase of newly created GABA at the synaptic junction. If gabapentin does indeed increase GABA levels or the effectiveness of GABA at the synaptic junction, then it could be classified as a GABA-mimetic and might decrease or inhibit cerebral function and might, therefore, slow function and decrease mood leading to depression.

The fact that a GABA agonist or GABA-mimetic might work just the opposite way by increasing mood and thus, be an antidepressant, is a new concept, different from the prevailing opinion of GABA activity heretofore.

The compounds of the instant invention are also expected to be useful in the treatment of anxiety and of panic as demonstrated by means of standard pharmacological procedures.

MATERIAL AND METHODS

Carrageenin-Induced Hyperalgesia

Nociceptive pressure thresholds were measured in the rat paw pressure test using an analgesimeter (Randall-Selitto method: Randall L. O. and Selitto J. J., "A method for measurement of analgesic activity on inflamed tissue," *Arch. Int. Pharmacodyn.*, 1957;4:409–419). Male Sprague-Dawley rats (70–90 g) were trained on this apparatus before the test day. Pressure was gradually applied to the hind paw of each rat and nociceptive thresholds were determined as the pressure (g) required to elicit paw withdrawal. A cutoff point of 250 g was used to prevent any tissue damage to the paw. On the test day, two to three baseline measurements were taken before animals were administered 100 $\mu$L of 2% carrageenin by intraplantar injection into the right hind paw. Nociceptive thresholds were taken again 3 hours after carrageenin to establish that animals were exhibiting hyperalgesia. Animals were dosed with either gabapentin (3–300 mg, s.c.), morphine (3 mg/kg, s.c.) or saline at 3.5 hours after carrageenin and nociceptive thresholds were examined at 4, 4.5, and 5 hours postcarrageenin.

(R)-2-Aza-spiro[4.5]decane-4-carboxylic acid hydrochloride was tested in the above carrageenan-induced hyperalgesia model. The compound was dosed orally at 30 mg/kg, and 1 hour postdose gave a percent of maximum possible effect (MPE) of 53%. At 2 hours postdose, it gave only 4.6% of MPE.

Semicarbazide-Induced Tonic Seizures

Tonic seizures in mice are induced by subcutaneous administration of semicarbazide (750 mg/kg). The latency to the tonic extension of forepaws is noted. Any mice not convulsing within 2 hours after semicarbazide are considered protected and given a maximum latency score of 120 minutes.

Animals

Male Hooded Lister rats (200–250 g) are obtained from Interfauna (Huntingdon, UK) and male TO mice (20–25 g) are obtained from Bantin and Kingman (Hull, UK). Both rodent species are housed in groups of six. Ten Common Marmosets;(Callithrix Jacchus) weighing between 280 and 360 g, bred at Manchester University Medical School (Manchester, UK) are housed in pairs. All animals are housed under a 12-hour light/dark cycle (lights on at 07.00 hour) and with food and water ad libitum.

Drug Administration

Drugs are administered either intraperitoneally (IP) or subcutaneously (SC) 40 minutes before the test in a volume of 1 mL/kg for rats and marmosets and 10 mL/kg for mice.

Mouse Light/Dark Box

The apparatus is an open-topped box, 45 cm long, 27 cm wide, and 27 cm high, divided into a small (2/5) and a large (3/5) area by a partition that extended 20 cm above the walls (Costall B., et al., "Exploration of mice in a black and white box: validation as a model of anxiety," *Pharmacol. Biochem. Behav.*, 1989;32:777–785).

There is a 7.5×7.5 cm opening in the center of the partition at floor level. The small compartment is painted black and the large compartment white. The white compartment is illuminated by a 60-W tungsten bulb. The laboratory is illuminated by red light. Each mouse is tested by placing it in the center of the white area and allowing it to explore the novel environment for 5 minutes. The time spent in the illuminated side is measured (Kilfoil T., et al., "Effects of anxiolytic and anxioenic drugs on exploratory activity in a simple model of anxiety in mice," *Neuropharmacol.*, 1989;28:901–905).

Rat Elevated X-Maze

A standard elevated X-maze (Handley S. L., et al., "Effects of alpha-adrenoceptor agonists and antagonists in a maze-exploration model of 'fear'-motivated behavior," *Naunyn-Schiedeberg's Arch. Pharmacol*, 1984;327:1–5), was automated as previously described (Field, et al., "Automation of the rat elevated X-maze test of anxiety," *Br. J Pharmacol.*, 1991; 102(Suppl.):304P). The animals are placed on the center of the X-maze facing one of the open arms. For determining anxiolytic effects the entries and time spent on the end half sections of the open arms is measured during the 5-minute test period (Costall, et al., "Use of the elevated plus maze to assess anxiolytic potential in the rat," *Br. J Pharmacol.*, 1989;96(Suppl.):312p).

Marmoset Human Threat Test

The total number of body postures exhibited by the animal towards the threat stimulus (a human standing approximately 0.5 m away from the marmoset cage and staring into the eyes of the marmoset) is recorded during the 2-minute test period. The body postures scored are slit stares, tail postures, scent marking of the cage/perches, piloerection, retreats, and arching of the back. Each animal is exposed to the threat stimulus twice on the test day before and after drug treatment. The difference between the two scores is analyzed using one-way analysis of variance followed by Dunnett's t-test. All drug treatments are carried out SC at least 2 hours after the first (control) threat. The pretreatment time for each compound is 40 minutes.

Rat Conflict Test

Rats are trained to press levers for food reward in operant chambers. The schedule consists of alternations of four 4-minute unpunished periods on variable interval of 30 seconds signaled by chamber lights on and three 3-minute punished periods on fixed ratio 5 (by footshock concomitant to food delivery) signaled by chamber lights off. The degree of footshock is adjusted for each rat to obtain approximately 80% to 90% suppression of responding in comparison with unpunished responding. Rats receive saline vehicle on training days.

DBA2 Mouse Model of Anticonvulsant Efficacy

All procedures were carried out in compliance with the NIH Guide for the Care and Use of Laboratory Animals under a protocol approved by the Parke-Davis Animal Use Committee. Male DBA/2 mice, 3 to 4 weeks old were obtained from Jackson Laboratories, Bar Harbour, Me. Immediately before anticonvulsant testing, mice were placed upon a wire mesh, 4 inches square, suspended from a steel rod. The square was slowly inverted through 180° and mice observed for 310 seconds. Any mouse falling from the wire mesh was scored as ataxic (Coughenour L. L., McLean J. R., Parker R. B., "A new device for the rapid measurement of impaired motor function in mice," *Pharm. Biochem. Behav.*, 1977;6(3):351–3). Mice were placed into an enclosed acrylic plastic chamber (21 cm height, approximately 30 cm diameter) with a high-frequency speaker (4 cm diameter) in the center of the top lid. An audio signal generator (Protek model B-810) was used to produce a continuous sinusoidal tone that was swept linearly in frequency between 8 kHz and 16 kHz once each 10 msec. The average sound pressure level (SPL) during stimulation was approximately 100 dB at the floor of the chamber. Mice were placed within the chamber and allowed to acclimatize for one minute. DBA/2 mice in the vehicle-treated group responded to the sound stimulus (applied until tonic extension occurred, or for a maximum of 60 sec) with a characteristic seizure sequence consisting of wild running followed by clonic seizures, and later by tonic extension, and finally by respiratory arrest and death in 80% or more of the mice. In vehicle-treated mice, the entire sequence of seizures to respiratory arrest lasts approximately 15 to 20 seconds. The incidence of all the seizure phases in the drug-treated and vehicle-treated mice was recorded, and the occurrence of tonic seizures were used for calculating anticonvulsant $ED_{50}$ values by probit analysis (Litchfield J. T., Wilcoxon F. "A simplified method for evaluating dose-effect experiments," *J. Pharmacol.*, 1949;96:99–113). Mice were used only once for testing at each dose point. Groups of DBA/2 mice (n=5–10 per dose) were tested for sound-induced seizure responses 2 hours (previously determined time of peak effect) after given drug orally. All drugs in the present study were dissolved in distilled water and given by oral gavage in a volume of 10 mL/kg of body weight. Compounds that are insoluble will be suspended in 1% carboxymethocellulose. Doses are expressed as weight of the active drug moiety.

The compounds of the instant invention are also expected to be useful in the treatment of pain and phobic disorders (*Am. J Pain Manag.*, 1995;5:7–9).

The compounds of the instant invention are also expected to be useful in treating the symptoms of manic, acute or chronic, single upside, or recurring depression. They are also expected to be useful in treating and/or preventing bipolar disorder (U.S. Pat. No. 5,510,381).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the; like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 1 g according to the particular application and the potency of the active component. In medical use the drug may be administered three times daily as, for example, capsules of 100 or 300 mg. The composition can, if desired, also contain other compatible therapeutic agents.

In therapeutic use, the compounds utilized in the pharmaceutical method of this invention are administered at the initial dosage of about 0.01 mg to about 100 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following examples are illustrative of the instant invention; they are not intended to limit the scope.

EXAMPLE 1

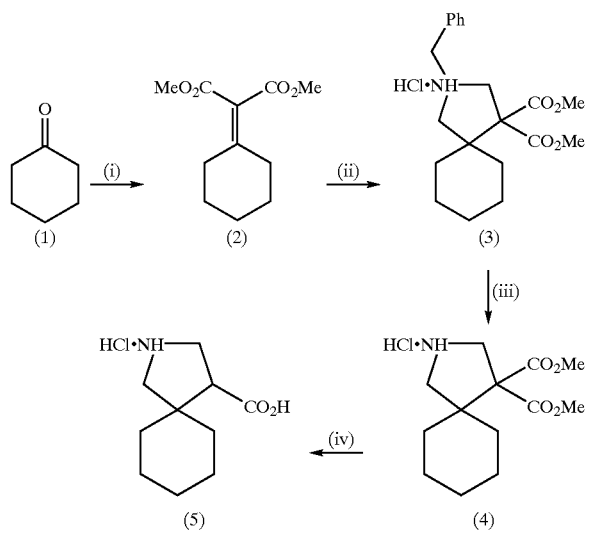

Reagents:
(i) $TiCl_4$, $MeO_2CCH_2CO_2Me$, pyridine, tetrahydrofuran;
(ii) N-Benzylglycine hydrochloride, $Et_3N$, paraformaldehyde, PhH;
(iii) Pearlman's catalyst, methanol, $H_2$;
(iv) 6N HCl.

2-Cyclohexylidene-malonic Acid Dimethyl Ester (2)

To 20 mL of tetrahydrofuran cooled at −78° C. was slowly added, under an argon atmosphere, $TiCl_4$ (1 M in $CH_2Cl_2$; 100 mL; 100 mmol). After the addition was complete, the reaction mixture was warmed up to −10° C. To the mixture was then successively added dimethylmalonate (6.73 g; 51 mmol), cyclohexanone 1 (5 g; 51 mmol) over 5 minutes and pyridine (16.4 mL; 201 mmol) over 1 hour 30 minutes. The brown suspension was then allowed to warm up to room temperature, stirred overnight and diluted with water (50 mL). The phases were separated, and the organic phase was washed with water, dried over $MgSO_4$, and the solvent removed in vacuo. The crude oil was chromatographed over silica gel (ether/heptane 1:1) to give 2 as a pale yellow solid (6.35 g; 30 mmol; 58%).

$^1$H NMR (CDCl$_3$) δ ppm: 1.6 (m, 6H); 2.5 (m, 4H); 3.75 (s, 6H). MS ES+[MW+1]$^+$: 213.

2-Benzyl-2-aza-spiro[4.5]decane-4,4-dicarboxylic Acid Dimethyl Ester Hydrochloride (3)

A solution of dimethyl (cyclohexylidene) malonate 2 (594 mg; 2.8 mmol), N-benzylglycine hydrochloride (1.41 g; 6.99 mmol), triethylamine (0.97 mL; 6.95 mmol), and paraformaldehyde (671 mg; 22.36 mmol) in benzene (18 mL) was slowly heated up to 125° C. (oil bath) (Dean-Stark). After stirring for 2 hours, the reaction mixture was cooled to room temperature, diluted with toluene (20 mL), and washed with brine. The aqueous phase was extracted with toluene (2×10 mL). The organic phases were combined, dried over $MgSO_4$, and evaporated to give a brown oil which was purified on silica gel chromatography (EtOAc/heptane 1:3). The resulting pale yellow oil was diluted in diethyl ether (10 mL), and the compound was extracted with 2N HCl (2×5 mL). The aqueous phases were combined, washed with diethyl ether, and concentrated in vacuo to give 3 as a white solid (238 mg; 0.62 mmol; 22%).

$^1$H NMR (D$_2$O) δ ppm: 1.2 to 1.9 (m, 10H); 3.65 and 3.9 ([AB]q, 2H); 3.9 (d, 6H); 4.1 and 4.25 ([AB]q, 2H); 4.65 (s, 2H); 7.6 (m, 5H). MS ES+[MW+1]$^+$: 3146.

2-Aza-spiro[4.5]decane-4,4-dicarboxylic Acid Dimethyl Ester Hydrochloride (4)

A solution of 3 (238 mg; 0.62 mmol) and 10% Palladium hydroxide on carbon (47 mg; 20% w/w) in methanol (10 mL) was stirred overnight at 40° C. under a hydrogen atmosphere (55 psi). The catalyst was filtered off through a celite pad, and the filtrate was evaporated under vacuum to give 4 as a yellow solid (170 mg; 0.58 mmol; 93%).

$^1$H NMR (D$_2$O) δ ppm: 1.2 to 1.8 (m, 10H); 3.65 (s, 2H); 3.9 (s, 6H); 4.01 (s, 2H). MS ES+[MW+1]$^+$: 256.

2-Aza-spiro[4.5]decane-4-carboxylic Acid Hydrochloride (5)

A solution of 4 (170 mg; 0.58 mmol) in 6N HCl (5 mL) was stirred overnight at 145° C. After cooling, the solvent was removed under vacuum to yield 5 as a pale yellow solid (153 mg; 0.58 mmol; quant.).

$^1$H NMR (D$_2$O) δ ppm: 1.39 to 1.8 (m, 10H); 3.1 (t, 1H); 3.4 ([AB]q, 2H); 3.7 (d[AB]q, 2H). MS ES+[MW+1]$^+$: 184. C,H,N Calc. for $C_{10}H_{17}NO_2$.1.75 HCl.1.00H$_2$O: C, 45.31; H, 7.89; N, 5.28. Observed: C, 45.65; H, 7.69; N, 5.62.

EXAMPLE 1A

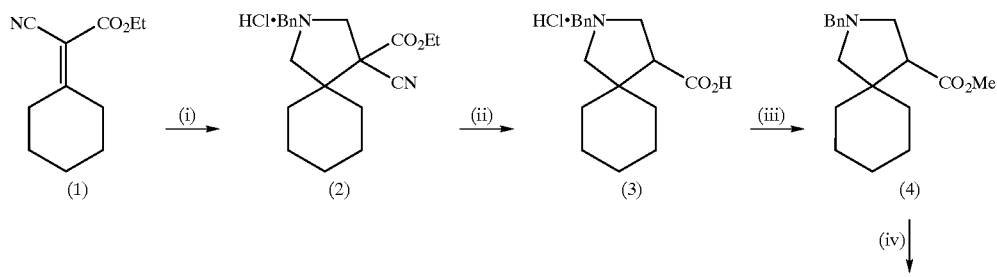

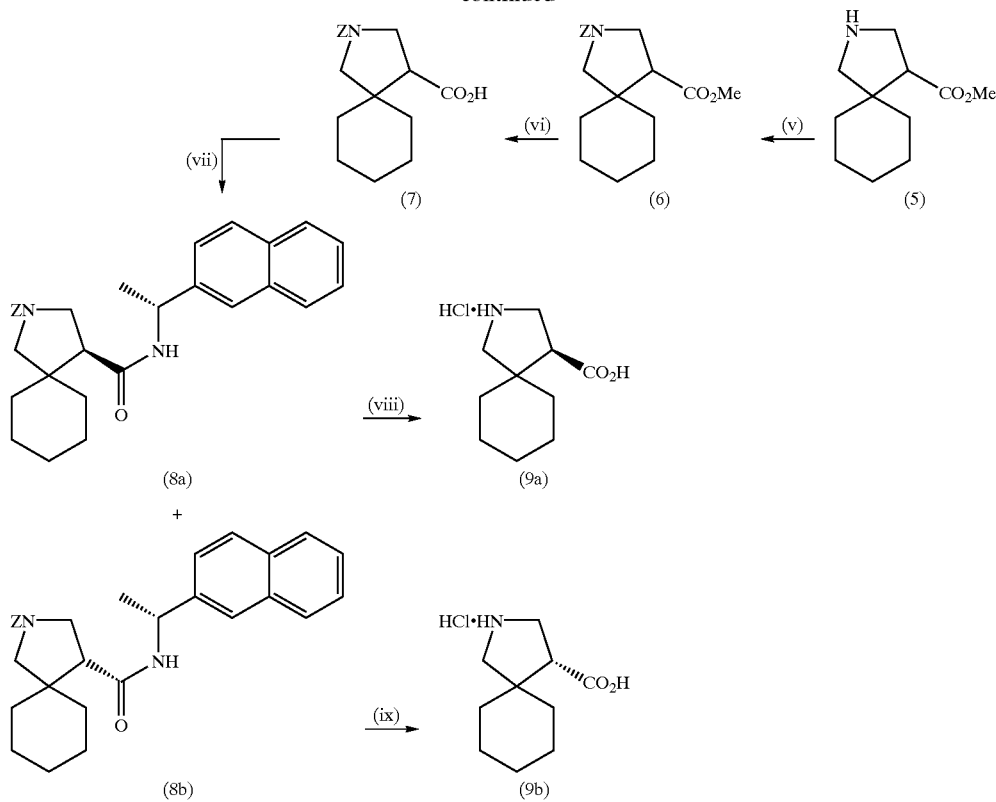

Bn = PhCH$_2$—, Z = PhCH$_2$OCO—

Reagents:
  5 (i) HCl.BnNHCH$_2$CO$_2$H, Et$_3$N, HCHO, PhH, reflux (82%);
  (ii) 6N HCl reflux (94%);
  (iii) MeOH, HCl, reflux (65%);
  (iv) Pd(OH)$_2$/C, H$_2$, MeOH (97%);
  (v) BnOCOCl, Py, CH$_2$Cl$_2$, (88%);
  (vi) Dioxane/Aq NaOH (89%);
  (vii) CH$_2$Cl$_2$, (COCl)$_2$, HCONMe$_2$ then (R)-(+)-1-(2-Napthyl)ethylamine followed by flash chromatography (20a)—43% and (20b)—39%;
  (viii) 6N HCl, THF reflux (73%);
  (ix) 6N HCl, THF reflux (78%).

2-Benzyl-2-aza-spiro[4.5]decane-4-carboxylic Acid Methyl Ester (4)

A solution of (1) (4 g; 20.70 mmol), N-benzylglycine hydrochloride (10.4 g; 51.57 mmol),triethylamine (7.2 mL; 51.65 mmol), and paraformaldehyde (5.2 g; 173.30 mmol) in benzene (120 mL) was refluxed for 2 hours using a Dean-Stark apparatus. After cooling, the reaction mixture was diluted with toluene (200 mL) and washed with brine. The aqueous phase was extracted with toluene (3×30 mL). The organic extracts were combined, dried over MgSO$_4$, and concentrated in vacuo. The crude oil was purified over silica-gel chromatography in EtOAc/heptane (1:3) to give a yellow oil which was diluted in ether (30 mL) and extracted with 3N HCl (3×25 mL). The aqueous phase was washed with ether (2×30 mL) and was concentrated under vacuum to give (2) as a white powder (6.20 g; 17.08 mmol) which was used without any further purification. A solution of (2) (6.2 g; 17.08 mmol) in 6N HCl (120 mL) was refluxed overnight. Evaporating the solvent in vacuo gave 5 g (16.13 mmol; 77% from (1)) of (3) as a pale yellow solid which was immediately esterified. Acetyl chloride (5 mL; 70.32 mmol) was slowly added to methanol (100 mL), at 0° C., under an argon atmosphere. After stirring for 10 minutes, this solution was transferred to a flask containing (3) (5 g; 16.13 mmol), under an argon atmosphere. The reaction mixture was then stirred at 95° C. for 3 hours. After cooling, the methanol was removed in vacuo. The residue was basified with saturated aqueous Na$_2$CO$_3$, and was extracted with ether (3×30 mL). The organic phases were combined, dried over MgSO$_4$, and concentrated to give 3 g (10.44 mmol; 50% from (1)) of (4) as a pale yellow liquid.

$^1$H NMR (CDCl$_3$) 400 MHz δ: 1.0 to 1.7 (m, 10H); 2.25 (d, 1H); 2.65 to 2.9 (m, 4H); 3.6 ([AB]q, 2H); 3.65 (s, 3H, OCH$_3$)); 7.3(m, 5H, Ph). MS (ES$^+$) m/e: 288 ([MH]$^+$,100%).

2-Aza-spiro[4.5]decane-2,4-dicarboxylic Acid 2-Benzyl Ester 4-Methyl Ester (6)

A solution of (4) (3 g; 10.44 mmol) and 10% Pd (OH)$_2$/C (0.60 g; 20% w/w) in methanol (50 mL) was stirred for 24 hours at 40° C. under at atmosphere of dry hydrogen gas. The catalyst was filtered off through a celite pad, and the filtrate was concentrated in vacuo to.give 2 g (10.14 mmol; 97%) of (5) as a colorless oil which was used without any further purification. To a solution of (5) (2 g; 10.14 mmol) in dry dichloromethane (100 mL) was successively added, at 0° C., under an argon atmosphere, pyridine (2.04 mL; 25.35 mmol), and benzylchloroformate (2.89 mL; 20.24 mmol). The reaction mixture was then allowed to stir at room temperature for 2 days. The reaction mixture was washed (2×50 mL) with 1N HCl, dried over MgSO$_4$, and concentrated in vacuo. The crude oil was purified by silica-gel flash chromatography in ether/heptane (1:1) to give 2.97 g (8.96 mmol; 88%) of (6) as a colorless oil.

¹H NMR (CDCl₃) 400 MHz δ: 1.15 to 1.7 (m, 10H); 2.8 (m, 1H); 3.3 (m, 1H); 3.45 to 3.8 (m, 6H); 5.15 ([AB]q, 2H, PhC$\underline{H}$₂); 7.3 (m, 5H, Ph). MS (ES⁺) m/e: 332 ([MH]⁺, 100%).

2-Aza-spiro[4.5]decane-2,4-dicarboxylic Acid 2-Benzyl Ester (7)

To a solution of (6) (300 mg; 0.9 mmol) in a mixture dioxane/water (6 mL; 9:1) was added a 2 M solution of NaOH (0.90 mL; 1.8 mmol). The reaction mixture was stirred at 35° C. for 6 hours. Solvents were removed in vacuo. The residue was diluted in water (15 mL) and was washed with diethyl ether (3×10 mL). The aqueous phase was acidified with 2N HCl and was extracted with ethyl acetate (3×15 mL). The ethyl acetate extracts were combined, dried over MgSO₄, and concentrated to give 254 mg (0.8 mmol; 89%) of (7) as a colorless gum.

¹H NMR (CDCl₃) 400 MHz δ: 1.2 to 1.75 (m, 10H); 2.8 (m, 1H); 3.3 (m, 1H); 3.5 to 3.8 (m, 3H); 5.1 (ABq, 2H); 7.3 (m, 5H). MS (ES⁺) m/e: 318 ([MH]⁺, 100%).

(4S,1'R)-4-(1'-Naphthalen-2-yl-ethylcarbamoyl)-2-aza-spiro[4.5]decane-2-carboxylic Acid Benzyl Ester (8a) and (4R,1'R)4-(1'-Naphthalen-2-yl-ethylcarbamoyl)-2-aza-spiro[4.5]decane-2-carboxylic Acid Benzyl Ester (8b)

To a cooled (0° C.) solution of (7) (1.71 g; 5.38 mmol) in dry dichloromethane (35 mL) were successively added, under an argon atmosphere, oxalyl chloride (0.56 mL; 6.42 mmol) and dimethylformamide (20 µL; 0.26 mmol). The reaction mixture was stirred at 0° C. for 30 minutes and then was allowed to stir at room temperature for 2 hours. The solvent was removed in vacuo, and the residue was diluted in dry dichloromethane (35 mL). This solution was then added to a solution of (R)-(+)-1-(2-naphthyl)ethylamine (1.10 g; 6.42 mmol) and triethylamine (0.90 mL; 6.42 mmol) in dry dichloromethane (50 mL) under an argon atmosphere. The reaction mixture was stirred at room temperature overnight. 2N HCl (30 mL) was added, and the organic and aqueous phases were separated. The organic phase was washed with water (30 mL), dried over MgSO₄, and concentrated to give a pale yellow oil which was purified over silica-gel chromatography in EtOAc/heptane (1:1) to give 1.1 g (2.34 mmol; 43%) of (8a) and 1.0 g (2.12 mmol; 39%) of (8b) as white solids.

¹H NMR (CDCl₃) 400 MHz δ: (8a): 1.2 to 1.65 (m, 13H); 2.4 (m, 1H); 3.35 (d, 1H); 3.5 to 3.8 (m, 3H); 5.1 (m, 2H); 5.3 (m, 1H); 5.7 (t, 1H); 7.3 to 7.8 (m, 12H). (8b): 1.2 to 1.65 (m, 13H); 2.4 (m, 1H); 3.25 (d, 1H); 3.5 to 3.8 (m, 3H); 5.1 (m, 2H); 5.3 (m, 1H); 5.7 (t, 1H); 7.3 to 7.8 (m, 12H). MS (ES⁺) m/e: (8a): 471 ([MH ]⁺, 100%); (8b): 471 ([MH ]⁺, 100%).

(S)-2-Aza-spiro[4.5]decane4-carboxylic Acid (9a)

To a solution of (8a) (770 mg; 1.64 mmol) in THF (5 mL) was added 6N aqueous HCl (40 mL). The reaction mixture was stirred under reflux overnight. After cooling, the reaction mixture was washed with EtOAc (2×20 mL). The phases were separated, and the aqueous phase was concentrated to dryness under vacuum. The crude residue was dissolved in 6N aqueous HCl (40 mL), and the reaction mixture was stirred under reflux for 60 hours. After cooling, the reaction mixture was washed with EtOAc (2×20 mL). The phases were separated, and the aqueous phase was! concentrated to dryness to leave a solid which was dissolved in water. Removing water under vacuum led to (9a) as a white powder (263 mg; 1.20 mmol; 73%).

¹H NMR (CDCl₃) 400 MHz δ: 1.2 to 1.8 (m, 10H); 3.1 (t, 1H); 3.4 ([AB]q, 2H); 3.7 (m, 2H). MS (ES⁺) m/e: 184 ([MH]⁺, 100%).

(R)-2-Aza-spiro[4.5]decane4-carboxylic Acid (9b)

(8b) (553 mg; 1.17 mmol) was converted to 200 mg (0.91 mmol; 78%) of (12b) by the same procedure for (9a) to (12a).

¹H NMR (CDCl₃) 400 MHz δ: 1.2 to 1.8 (m, 10H); 3.1 (t, 1H); 3.4 ([AB]q, 2H); 3.7 (m, 2H). MS (ES⁺) m/e: 184 ([MH]⁺, 100%).

EXAMPLE 2

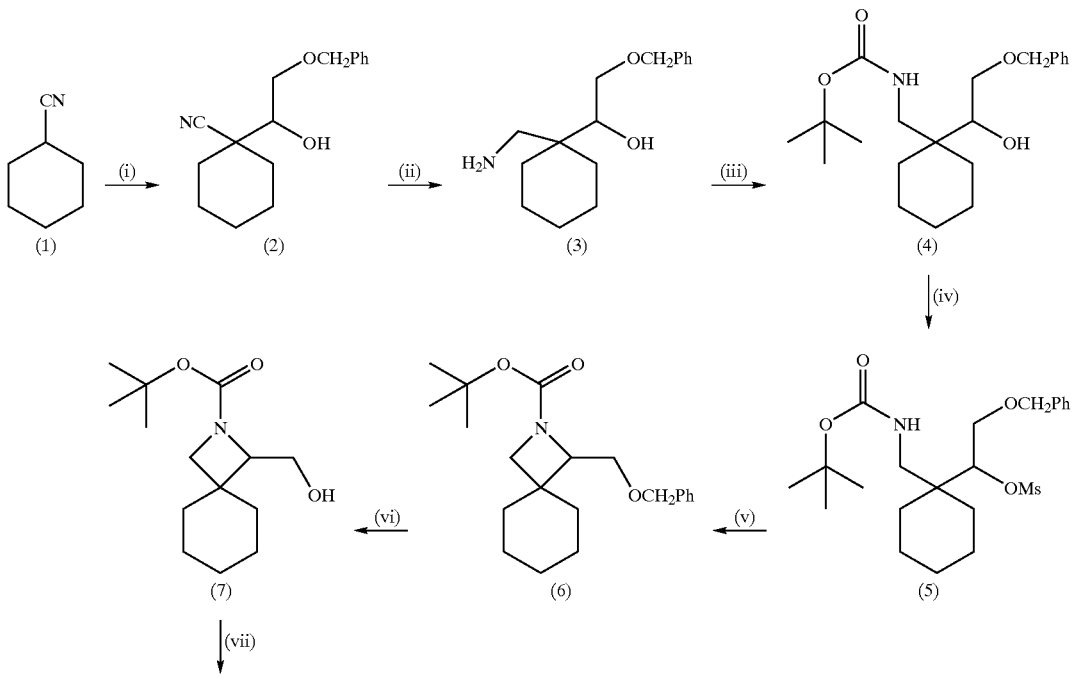

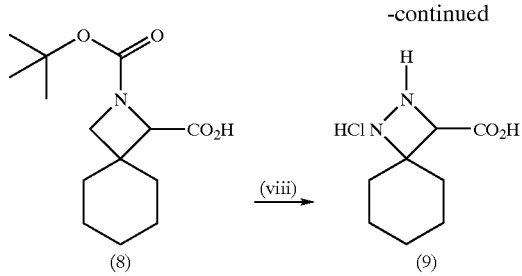

Reagents:
(i) BnOCH$_2$CHO, LiN(iPr)$_2$, THF, −78° C. to −20° C.;
(ii) AlCl$_3$, LiAlH$_4$, Et$_2$O;
(iii) BOC$_2$ O. dichloromethane;
(iv) MeSO$_2$Cl, Et$_3$N, dichloromethane;
(v) NaH, dimethylformamide;
(vi) Ammonium formate, 10% Pd/C, MeOH;
(vii) NalO$_4$, RuCl$_3$, CCl$_4$, CH$_3$CN, H$_2$O;
(viii) IN HCl (g) in ethyl acetate.

1-(2-Benzyloxy-1-hydroxy-ethyl)-cyclohexanecarbonitrile (2)

Lithium diisopropylamide was prepared by dropwise addition of n-BuLi (2.03 mL; 2.5 M in Hexanes; 5.08 mmol) to a stirred and cooled (−10° C.) solution of i-Pr$_2$NH (0.84 mL; 6.0 mmol) in dry tetrahydrofuran (40 mL). Stirring was continued for 20 minutes. The mixture was cooled to −78° C. and cyclohexane carbonitrile 1 (500 mg; 4.62 mmol) was added over 5 minutes. After a further 30 minutes, benzyloxyacetaldehyde (0.97 mL; 6.93 mmol) was added dropwise. Stirring was continued at −78° C. for 7 hours. The reaction mixture was then allowed to stir overnight at −20° C. Saturated aqueous NH$_4$Cl was added (10 mL), and the mixture was extracted with diethyl ether (2×20mL), dried over MgSO$_4$ and evaporated. The residue was purified over silica gel chromatography (ether/heptane 1:1) to give 2 as a white solid (872 mg; 3.37 mmol; 73%)
$^1$H NMR (CDCl$_3$) δ: 1.1 to 1.8 (m, 9H); 2.2 (d, 1H); 2.75 (s, 1H); 3.6 to 3.8 (m, 3H); 4.6 ([AB]q, 2H); 7.4 (m, 5H). MS ES+[MW+1]$^+$: 259.

1-(1-Aminomethyl-cyclohexyl)-2-benzyloxy-ethanol (3)

To AlCl$_3$ (410 mg; 3.07 mmol) was added, at −78° C. and under an argon atmosphere, 3 mL of diethyl ether. The dry ice-bath was removed. The mixture was stirred at room temperature for 10 minutes, and then was added to LiAlH$_4$ (3.02 mL; 1 M in diethyl ether; 3.02 mmol). A solution of 2 (300 mg; 1.16 mmol) in diethyl ether (3 mL) was then added over the course of 2 minutes, and the reaction mixture was stirred overnight at room temperature. The mixture was quenched by cautious addition of water (2 mL) followed by addition of 10% H$_2$SO$_4$ (30 mL). The aqueous phase was washed with diethyl ether (3×15 mL), basified with NaOH pellets (excess) and extracted with diethyl ether (3×15 mL). The organic phases were combined, washed with brine, dried over MgSO$_4$, and evaporated to give 3 as a colorless oil (230 mg; 0.87 mmol; 76%) which was used without further purification.
$^1$H NMR (CDCl$_3$) δ ppm: 1.2 to 1.7 (m, 10H); 2.75 (d, 1H); 2.95 (s, 1H); 3.6 (dd, 1H); 3.7 (dd, 1H); 4.6 ([AB]q, 2H); 7.3 (m, 5H). MS ES+[MW+1]$^+$: 264.

[1-(2-Benzyloxy-1-hdroxy-ethyl)-cyclohexylmethyl]-carbamic Acid Tert-butyl Ester (4)

A solution of 3 (244 mg; 0.92 mmol) and BOC$_2$O (242 mg; 1.11 mmol) in CH$_2$Cl$_2$ (8 mL) was stirred at room temperature for 24 hours under an argon atmosphere. The solvent was removed under vacuum, and the crude oil was purified over silica gel chromatography (ether/heptane 1:1) to give 4 as a colorless oil (298 mg; 0.82 mmol; 89%).
$^1$H NMR (CDCl$_3$) δ ppm: 1.1 to 1.6 (m, 10H); 1.4 (s, 9H); 2.8 (s, 1H); 3.1 (dd, 1H); 3.35 (dd, 1H); 3.5 (t, 1H); 3.65 (dd, 1H); 3.75 (dd, 1H); 4.6 ([AB]q, 2H); 5.5 (bs, 1H); 7.3 (m, 5H). MS ES+[MW+1]$^+$: 364.

Methanesulfonic Acid 2-Benzyloxy-1-[1-(tert-butoxycarbonylamino-methyl)-cyclohexyl]-ethyl ester (5)

To a cooled (−10' C.) solution of 4 (290 mg; 0.79 mmol) and triethylamine (0.33 mL; 2.39 mmol), in CH$_2$Cl$_2$ (5 mL) was added, under an argon atmosphere, MsCl (0.154 mL; 1.93: mmol) diluted in CH$_2$Cl$_2$ (0.5 mL). The reaction mixture was then allowed to stir at room temperature for 2 days. The solvent was removed under vacuum, and the residue was diluted in diethyl ether, washed with water, dried over MgSO$_4$, and concentrated. The crude oil was purified over silica gel chromatography (ether/heptane 1:1) to give 5 as a colorless oil (200 mg; 0.45 mmol; 57%)
$^1$H NMR (CDCl$_3$) δ ppm: 1.2 to 1.6 (m, 10H); 1.2 (s, 9H); 3 (s, 1H); 3.05 (dd, 1H); 3.25 (dd, 1H); 3.8 (m, 2H); 4.55 ([AB]q, 2H); 4.75 (m, 1H); 5.05 (m, 1H); 7.3 (m, 5H). MS ES+[MW+1]$^+$: 442

1-Benzyloxymethyl-2-aza-spiro[3.5]nonane-2-carboxylic Acid tert-butyl Ester (6)

A solution of 5 (2.53 g; 5.73 mmol) and NaH (460 mg; 60% w/w in oil; 11.47 mmol) in dry DI4F (115 mL) was stirred at 45° C. for 1 hour under an argon atmosphere. The reaction was quenched by cautious addition of saturated NH$_4$Cl (200 mL), and the aqueous phase was extracted with diethyl ether (2×100 mL). The organic phases were combined, dried over MgSO$_4$, and evaporated. The residue was purified over silica gel chromatography (ether/heptane 1:2) to give 6 as a colorless oil (1.20,g; 3.48 mmol; 59%).
$^1$H NMR (CDCl$_3$) δ ppm: 1.2 to 1.8 (m, 10H); 1.4 (s, 9H); 3.45 ([AB]q, 2H); 3.7 (m, 2H); 3.85 (m, 1H); 4.55 ([AB]q, 2H); 7.3 (m, 5H). MS ES+[MW+1]$^+$: 346.

1-Hydroxymethyl-2-aza-spiro[3.5]nonane-2-carboxylic Acid Tert-butyl Ester (7)

A solution of 6 (349 mg; 1.01 mmol), ammonium formate (638 mg; 10.1 mmol) and 10% Pd/C (349 mg; 1 eq. w/w) in methanol (20 mL) was heated to reflux for 2 hours. Ammonium formate (638 mg; 10.1 mmol) and 10% Pd/C (175 mg; 0.5 eq. w/w) were added, and the reaction mixture was refluxed for a further 2 hours. After cooling, the catalyst was filtered off through a celite pad, and the filtrate was evaporated. The crude oil was purified over silica gel chromatography (ether /heptane 4:1) to give 7 as a white solid (193 mg; 0.76 mmol; 75%).
$^1$H NMR (CDCl$_3$) δ ppm: 1.1 to 1.8 (m, 10H); 1.45 (s, 9H); 3.55 ([AB]q, 2H); 3.7 (m, 1H); 3.9 (m, 2H); 4.45 (bs, 1H). MS ES+[MW+1]$^+$: 256. C,H,N Calc.: C, 65.85; H. 9.87; N, 5.48. Observed: C, 65.54; H, 9.65; N, 5.39.

2-Aza-spiro[3.5]nonane-1,2-dicarboxylic Acid 2-Tert-butyl Ester (8)

To 7 (212 mg; 0.83 mmol) dissolved in a mixture of $CCl_4$ (1.7 mL), $CH_3CN$ (1.7 mL), and water (2.5 mL) was added $NaIO_4$ (710 mg; 3.32 mmol). After 15 minutes, hydrated $RuCl_3$ (4.8 mg; 2.2% mol) was added, and the reaction mixture was stirred at room temperature for 2 hours. The mixture was then extracted with $CH_2Cl_2$ (3×5 mL), washed with water, dried over $MgSO_4$ and concentrated. The crude oil was diluted in diethyl ether (5 mL) and saturated aqueous $Na_2CO_3$ (5 mL) was added. The aqueous phase was washed with diethyl ether (3×5 mL), acidified up to pH=3 with 1N HCl and extracted with diethyl ether (3×5 mL). The organic phases were combined, washed with water and concentrated in vacuo to give 8 as a white solid (185 mg; 0.69 mmol; 83%).

$^1$H NMR ($CDCl_3$) δ ppm: 1.2 to 1.8 (m, 10H); 1.5 (s, 9H); 3.6 ([AB]q, 2H); 4.3 (s, 1H). MS ES+[MW+1]$^+$: 270. C,H,N Calc.: C, 62.43; H, 8.60; N, 5.20. Observed: C, 62.40; H, 8.75; N, 5.01.

2-Aza-spiro[3.5]nonane-1-carboxylic Acid Hydrochloride (9)

Compound 8 (21.5 mg; 0.079 mmol) was dissolved in a dry 1 M HCl(g) solution in ethyl acetate (0.4 mL; 0.4 mmol) under an argon atmosphere. The reaction mixture was stirred at room temperature for 5 hours. The white precipitate was collected by filtration and washed several times with dry diethyl ether (2 mL) and dried under vacuum to give 9 as a white powder (15.2 mg; 0.074 mmol; 92%).

$^1$H NMR ($CDCl_3$) δ ppm: 1.03 to 1.84 (m, 10H); 3.7 ([AB]q, 2H); 4.4 (s, 1H). MS ES+[MW+1]$^+$: 170. MP: 163–165° C. C,H,N Calc. $C_9H_{15}NO_2$.1.0HCl: C, 52.55; H, 7.84; N, 6.81. Observed: C, 52.50; H, 7.74; N, 6.88.

EXAMPLE 3

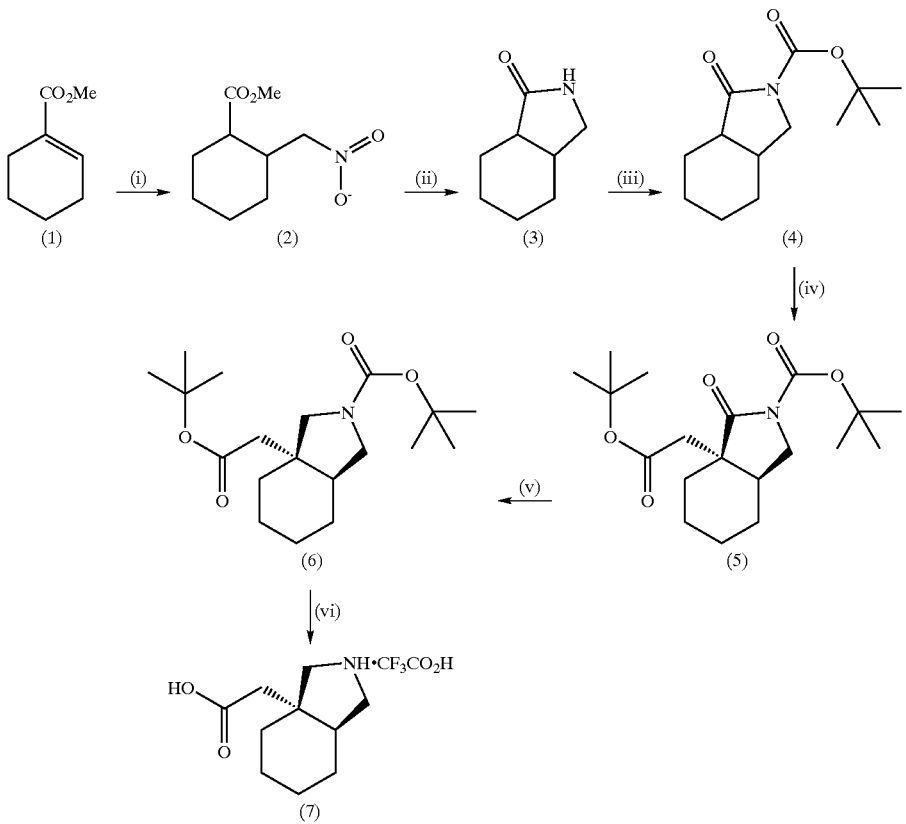

Reagents:
(i) $MeNO_2$, $(Bu)_4N^+F^-$; tetrahydrofuran;
(ii) Ni sponge, $H_2$, MeOH;
(iii) $(BOC)_2O$, 4-dimethylamino pyridine, $Et_3N$, tetrahydrofuran;
(iv) $LiN(iPr)_2$, $Me_3CO_2CCH_2Br$, tetrahydrofuran;
(v) $LiBHEt_3$, tetrahydrofuran then $Et_3SiH$, $BF_3.Et_2O$, dichloromethane;
(iv) $CF_3CO_2H$, dichloromethane.

2-Nitromethyl-cyclohexanecarboxylic Acid Methyl Ester (2)

A solution of cyclohex-1-enecarboxylic acid methyl ester 1 (5.15 g; 36.7 mmol), tetrabutyl ammonium fluoride (55.10 mL; 1 M in THF; 55.1 mmol) and nitromethane (3.97 mL; 73.5 mmol) in tetrahydrofuran (60 mL) was heated to reflux for 4 hours. After cooling to room temperature, the reaction mixture was diluted with diethyl ether (500 mL), washed with 2N HCl (2×100 mL) and then with brine (2×100 mL). The phases were separated. The organic phase was dried over $MgSO_4$ and concentrated in vacuo. The crude mixture was purified over silica gel chromatography (EtOAc/heptane 1:4) to give 2 (5.46 g; cis and trans isomers; 73%) as a pale yellow liquid.

$^1$H NMR 2 ($CDCl_3$) δ ppm: 1.1 to 2.4 (m, 10H); 3.7 (s, 3H); 4.25 (dd, 1H); 4.45 (dd, 1H). MS ES+[MW+1]$^+$: 202.

Octahydro-isoindol-1-one (3)

A solution of 2 (5.42 g; 27 mmol) and nickel sponge catalyst (cat.) in methanol (100 mL) was stirred at 30° C. for 4 hours under a hydrogen atmosphere (70 psi). The catalyst was filtered off through a celite pad, and the filtrate was concentrated under vacuum. Recrystallization of the crude solid (ether/heptane) gave 3 (3.69 g; 26.5 mmol; 98%) as a white powder.

$^1$H NMR ($CDCl_3$) δ ppm: 1.2 to 2.4 (m, 10H); 2.9 (d, 1H); 3.35 (m, 1H); 5.7 (bs, 1H). MS ES+[MW+1]$^+$: 140.

1-Oxo-octahydro-isoindole-2-carboxylic acid Tert-butyl ester (4)

To 3 (835 mg, 6 mmol) in suspension in tetrahydrofuran (7 mL) was successively added, under an argon atmosphere, 4-dimethylaminopyridine (18.3 mg; 0.15 mmol), triethylamine (0.84 mL; 6 mmol) and $BOC_2O$ (2.62 g; 12 mmol). The reaction mixture was stirred at room temperature for 3 days. The solvent was removed under vacuum. The residue was diluted with diethyl ether (20 mL) and washed with water (2×10 mL). The phases were separated, and the organic phase was dried over $MgSO_4$ and concentrated. The crude oil was purified over silica gel chromatography (ether/heptane 1:1) to give 4 (986 mg; 4.1 mmol; 70%) as a white solid.

$^1$H NMR ($CDCl_3$) δ ppm: 1.2 to 2.6 (m, 10H); 1.5 (s, 9H); 3.4 (d, 1H); 3.6 (dd, 1H). MS ES+[MW+1]$^+$: 240.

[3aS-(3α7aα)]-7a-tert-Butoxycarbonylmethyl-1-oxo-octahydro-isoindole-2-carboxylic acid Tert-butyl Ester (5)

Lithium diisopropylamide was prepared by dropwise addition of n-BuLi (1.39 mL; 2.5 M in hexanes; 3.47 mmol) to a stirred and cooled (−10° C.) solution of i-$Pr_2NH$ (0.63 mL; 4.5 mmol) in dry tetrahydrofuran (33 mL). Stirring was continued for 20 minutes. The mixture was cooled to −78° C. and 4 (832 mg; 3.47 mmol), dissolved in dry tetrahydrofuran (2 mL), was added over 5 minutes. After a further 30 minutes, tert-Butylbromoacetate (0.77 mL; 5.21 mmol) was added dropwise. The mixture was then allowed to warm up to room temperature. N,N-Dimethylpropyleheurea (5 mL; 41.3 mmol) was added, and the reaction mixture was heated up to 75° C. for 5 hours. After cooling, saturated $NH_4Cl$ (10 mL) was added, and the mixture was extracted with diethyl ether (2×20 mL). The phases were separated, and the organic phase was dried over $MgSO_4$ and concentrated. The residue was purified over silica gel chromatography (ether/heptane 1:1) to give 5 (840 mg; 2.37 mmol; 70%) as a colorless oil.

$^1$H NMR ($CDCl_3$) δ ppm: 1.2 to 1.7 (m, 8H); 1.4 (s, 9H); 1.55 (s, 9H); 2.5 (m, 1H); 2.55 [AB]q, 2H); 3.45 (dd, 1H); 3.75 (dd, 1H). MS ES+[MW+23]$^+$: 376.

[3aS-(α7aα)]-3a-tert-Butoxycarbonylmethyl-octahydro-isoindole-2-carboxylic Acid Tert-butyl Ester (6)

To a cooled (−78° C.) solution of 5 (340 mg; 0.96 mmol) in dry tetrahydrofuran (6 mL) was added, under an argon atmosphere, $LiBHEt_3$ (1.15 mL; 1 M in THF; 1.15 mmol). The reaction mixture was quenched after 4 hours by addition of saturated aqueous $NaHCO_3$ (1.8 mL). The mixture was allowed to warm up to 0° C. Thirty percent $H_2O_2$ (5 drops) was added, and the mixture was stirred at 0° C. for a further 30 minutes. The solvent was then removed under vacuum, and the aqueous phase was extracted with $CH_2Cl_2$ (3×5 mL). The organic phases were combined, dried over $MgSO_4$, and concentrated. To the crude residue in $CH_2Cl_2$ (15 mL) was added, at −78° C., under an argon atmosphere, $Et_3SiH$ (0.15 mL; 0.96 mmol) and $BF_3.Et_2O$ (0.135 mL; 1.05 mmol). After stirring for 30 minutes, a further $Et_3SiH$ (0.15 mL; 0.96 mmol) and $BF_3.Et_2O$ (0.135 mL; 1.05 mmol) were added, and the reaction mixture was stirred at −78° C. for 3 hours. Quenching was achieved at −78° C. by addition of saturated aqueous $NaHCO_3$ (1.5 mL). The phases were separated, and the organic phase was dried over $MgSO_4$ and concentrated. The residue was purified over silica gel chromatography ($Et_2O$/heptane 1:1) to give 6 (157 mg; 0.46 mmol; 48%) as a colorless oil.

$^1$H NMR ($CDCl_3$) δ ppm: 1.2 to 1.4 (m, 26H); 2 (m, 1H); 2.15 (d, 1H); 2.55 (dd, 1H); 3.2 to 3.5 (m, 4H). MS ES+[MW+1]$^+$: 340.

[3aS-(3α7aα)]-(Octaahydro-isoindol-3a-yl)-acetic acid trifluoroacetate (7)

A solution of 6 (100 mg; 0.29 mmol) in a mixture $CH_2Cl_2$/TFA (2 mL; 50:50) was stirred at room temperature for 2 hours. The solvent was removed under vacuum. The residue was diluted with water (2 mL) and washed with ether (2×2 mL). The phases were separated, and the aqueous phase was concentrated under vacuum to give 7 (60 mg; 0.17 mmol; 69%) as a pale yellow gum.

$^1$H NMR ($D_2O$) δ ppm: 1.4 to 1.8 (m, 8H); 2.3 (m, 1H); 2.5 (d, 1H); 2.95 (d, 1H); 3.35 to 3.95 (m, 4H). MS ES+[MW+1]$^+$: 184. C,H,N Calc. for $C_{10}H_{17}NO_2.1.0C_2HF_3O_2.0.7H_2O$: C, 46.51; H, 6.31; N, 4.52. Observed: C, 46.48; H, 5.98; N, 4.57.

The following compounds can also be prepared by the above synthetic methods:

7-Methyl-2-aza-spiro[4.4]nonane-4-carboxylic acid;

7,8-Dimethyl,2-aza-spiro[4.4]nonane-4-carboxylic acid;

7-Methyl-2-aza-spiro[4.5]decane-4-carboxylic acid;

7,9-Dimethyl-2-aza-spiro[4.5]decane-4-carboxylic acid;

Spiro [bicyclo[3.3.1]nonane-9,3'-pyrrolidine]-4'-carboxylic acid;

Spiro[pyrrolidine-3,2'-tricyclo[3.3.1.1$^{3,7}$]decane]-4-carboxylic acid;

3-Amino-6-methyl-spiro[3.5]nonane-1-carboxylic acid;

3-Amino-6,8-dimethyl-spiro[3.5]nonane-1-carboxylic acid;

4-Amino-7-methyl-spiro[4.5]decane-1-carboxylic acid;

4-Amino-7,9-dimethyl-spiro[4.5]decane-1-carboxylic acid;

3-Amino-6-methyl-spiro[3.4]octane-1-carboxylic acid;

3-Amino-6,7-dimethyl-spiro[3.4]octane-1-carboxylic acid;

4-Amino-7-methyl-spiro[4.4]nonane-1-carboxylic acid; and

4-Amino-7,8-dimethyl-spiro[4.4]nonane-1-carboxylic acid.

In all of the above compounds, all stereocenters may be R or S.

For example:

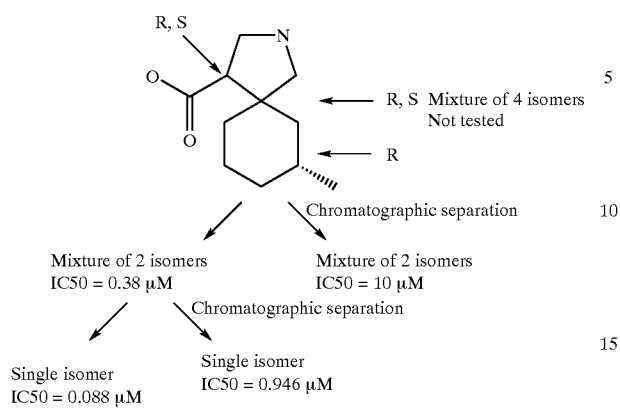

What is claimed is:
1. A compound of formula

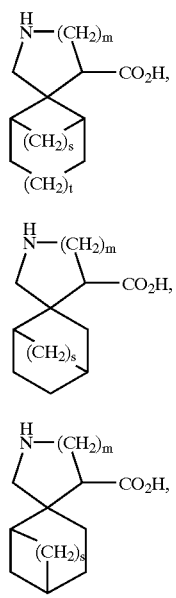

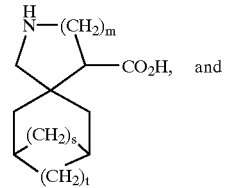

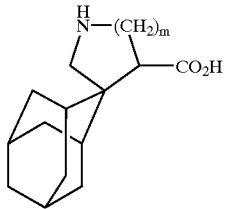

or a pharmaceutically acceptable salt thereof wherein m is 1;
s is an integer of from 1 to 3; and
t is an integer of from 0 to 2.

2. A compound selected from:
Spiro[bicyclo[3.3.1]nonane-9,3'-pyrrolidine]-4'-carboxylic acid; and
Spiro[pyrrolidine-3,2'-tricyclo[3.3.1.1$^{3,7}$]decane]-4-carboxylic acid.

3. A pharmaceutical composition comprising a therapeutically effective amount of a compound according to claim 1 and a pharmaceutically acceptable carrier.

4. A method for treating anxiety comprising administering a therapeutically effective amount of a compound according to claim 1 to a mammal in need of said treatment.

* * * * *